United States Patent [19]

Haeberli et al.

[11] 4,228,297

[45] Oct. 14, 1980

[54] PROCESS FOR THE PRODUCTION OF HYDROXYALKYLPHENYL DERIVATIVES

[75] Inventors: Joerg Haeberli, Warwick; Kyong P. Park, Cranston; Anthony F. Vellturo, N. Kingstown; George F. Nurnberger, Warwick, all of R.I.

[73] Assignee: Ciba-Geigy Corporation, Ardsley, N.Y.

[21] Appl. No.: 22,395

[22] Filed: Mar. 21, 1979

Related U.S. Application Data

[63] Continuation of Ser. No. 763,220, Jan. 27, 1977, abandoned, which is a continuation of Ser. No. 596,129, Jul. 15, 1975, abandoned, which is a continuation of Ser. No. 505,286, Sep. 12, 1974, abandoned, which is a continuation of Ser. No. 318,801, Dec. 27, 1972, abandoned.

[51] Int. Cl.$^2$ ............................................. C07C 69/76
[52] U.S. Cl. ................................. 560/75; 260/559 R; 546/226
[58] Field of Search ...................... 560/75; 260/559 R; 546/226

[56]  References Cited

U.S. PATENT DOCUMENTS

| | | | |
|---|---|---|---|
| 3,920,729 | 11/1975 | Sagawa | 260/473 S |
| 3,954,839 | 5/1976 | Dexter | 260/473 S |

*Primary Examiner*—Paul J. Killos
*Attorney, Agent, or Firm*—Joseph F. DiPrima; Harry Falber

[57]  ABSTRACT

An improved process for the production of hydroxyalkylphenyl derivatives, especially esters and amides containing hydroxyalkylphenyl groups is disclosed, which process comprises gradually adding methyl acrylate, in the presence of an alkaline catalyst, to the alkyl substituted phenolic compound, and adding to the resultant reaction mixture a suitable alcohol or amine, optionally in the presence of a second catalyst which is different from the first catalyst. The improved process results in good yields and in a reduction of undesirable by-products while avoiding isolation of the intermediates.

19 Claims, No Drawings

PROCESS FOR THE PRODUCTION OF HYDROXYALKYLPHENYL DERIVATIVES

This is a continuation of application Ser. No. 763,220 filed on Jan. 27, 1977, which is a continuation of application Ser. No. 596,129, filed on July 15, 1975, now abandoned; which is a continuation of application Ser. No. 505,286, filed Sept. 12, 1974, now abandoned; which is a continuation of application Ser. No. 318,801, filed Dec. 27, 1972, now abandoned.

DETAILED DISCLOSURE

Conventional methods for the production of different kinds of hydroxyalkylphenyl derivatives, particularly esters and amides thereof, involve multistep reaction procedures, such as transesterification of carboxylic acid-lower-alkyl esters containing hydroxyalylphenyl groups or amide formation. Said esters in their turn, are first prepared, e.g., by reacting corresponding alkylphenols with methyl acrylate, followed either by isolating the resultant intermediate ester and subsequent transesterification thereof or amide formation, or direct transesterification or amidization of the reaction product from the reaction melt. Isolation of the intermediate ester, though enabling production of the desired end product in good yields and reduction of by-products, requires the use of very substantial amounts of suitable solvents. The disposal of said solvents creates serious effluent problems under present day anti-pollution requirements. Direct transesterification or amidization of the reaction melt; on the other hand, results in the formation of considerable quantities of by-products, such as polymers and diesters, and hence in poor yields of the desired end-products.

The present invention provides an improved, simplified, process by which various kinds of esters and amides containing hydroxyalkyphenyl groups can be produced in good yields, without isolation of the intermediates, while undesirable by-products are kept at a minimum.

More specifically, the invention provides an improved process for the production of compounds having the formulae

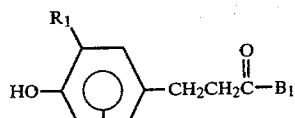   I,

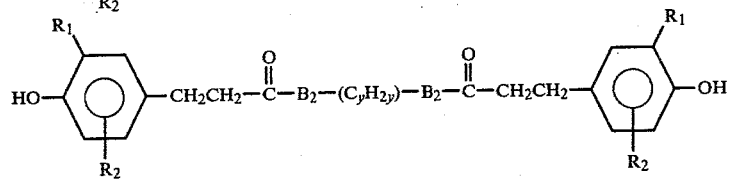   II,

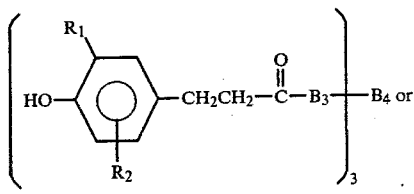   III

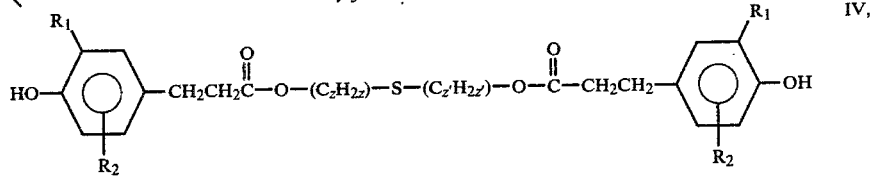   IV, in which formulae $R_1$ and $R_2$ independently of each other represent an alkyl group having from 1 to 6 carbon atoms;

$B_1$ represents $-O-(C_xH_{2x})-H$ or

wherein x has a value from 6 to 30, inclusively, $Y_1$ represents an alkyl group having from 1 to 18 carbon atoms or a cycloalkyl group having from 5 to 12 carbon atoms and $Y_2$ represents hydrogen or an alkyl group having from 1 to 18 carbon atoms, or a cycloalkyl group of 5 to 12 carbon atoms $Y_1$ and $Y_2$ together with the nitrogen atom to which they are linked form a piperidino ring, $B_2$ each represent $-O-$ or $-NH-$ and Y has a value from 2 to 10, inclusively, $B_3$ represents $-O-CH_2-$ and $B_4$ represents

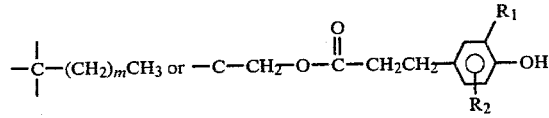

wherein $R_1$ and $R_2$ are as defined above, or and n is 0 to 6

$B_3$ represents $-NH-(CH_2)_m-$ and

B4 represents

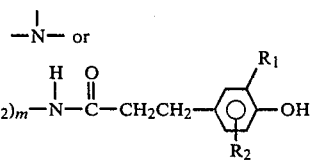

wherein n has a value from 2 to 6, inclusively, and $R_1$ and $R_2$ are as defined above, and each of s and s' have a balue from 2 to 12, inclusively, and, more especially esters having the formulae

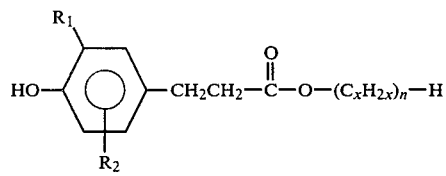

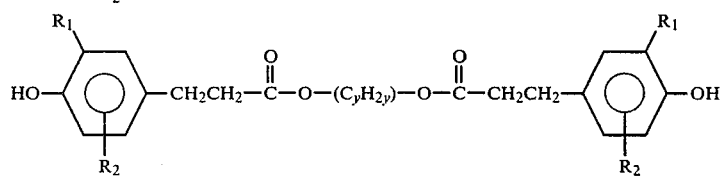

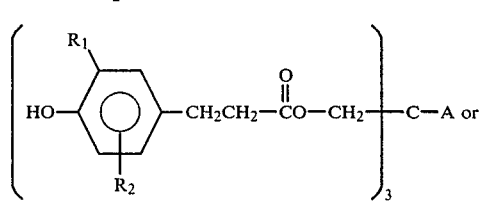

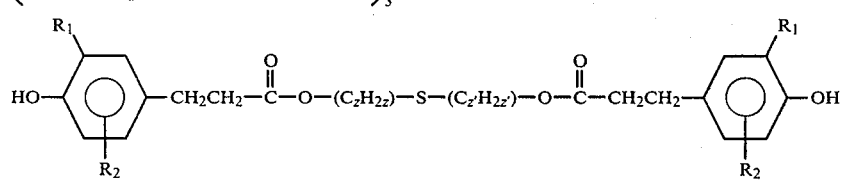

in which formulae:
$R_1$, $R_2$, x and y are as defined above,
each of z and z' have a value of 2 or 3, and
A represents —$CH_2CH_3$ or a radical of the formula

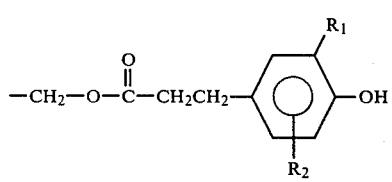

This process comprises gradually adding methyl acrylate to a phenol compound of the formula

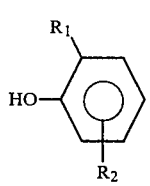

V wherein $R_1$ and $R_2$ are as defined above, in the presence of from 0.001 to 10 mole percent, based on the phenol compound of formula V, of an alkaline catalyst, and after completion of the reaction, adding to the resultant reaction mixture a compound selected from (a) a monohydric alcohol or a monoamine of the formulae $$HO(C_xH_{2x})-N \quad \text{or} \quad HN\diagup_{Y_2}^{Y_1}$$

Ia　　　　　Ib, (b) a dihydric alcohol or a diamine of the formulae $$HO-(C_yH_{2y})-OH \quad \text{or} \quad H_2N-(C_yH_{2y})-NH_2$$

IIa　　　　　　　　　　IIb, (c) a tri- or tetrahydric alcohol or a polyamine of the formulae $$(HO-B_3)_3-B_4' \quad \text{or} \quad (NH_2-B_3)_3-B_4''$$

IIIa　　　　　　　　IIIb, and (d) a thioether compound of the formula $$HO-(C_zH_{2z})-S-(C_{z'}H_{2z'})-OH \qquad \text{IVa,}$$

wherein
$R_1$, $R_2$, $B_3$, $Y_1$, $Y_2$, x, y, z and z' are as defined above, and
$B_4'$ represents

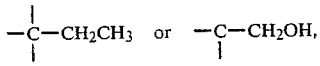

and

B₄'' represents

or >N—(CH₂)ₘ—NH
wherein m is as defined above, the second reaction being carried out in the presence of from 0 to 10 mole percent of a second alkaline catalyst which may be different from the first catalyst.

Alkyl groups represented by $R_1$ or $R_2$ can be straight or branched chained. Representative of such alkyl groups are thus methyl, ethyl, n-propyl, isopropyl, n-, sec- or tert-butyl, n-pentyl, sec-pentyl, neopentyl and n-hexyl. Preferably one, and most preferably both, of $R_1$ and $R_2$ are branched alkyl groups, such as isopropyl, and, more especially, tert-butyl. The alkyl radical designated by $R_2$ is either in a position para to $R_1$ or, preferably, in the other ortho position to the hydroxyl group.

Alkyl groups represented by $Y_1$ and/or $Y_2$ can also be straight or branched chain, examples thereof being methyl, ethyl, n- and isopropyl, n-, sec- and tert-butyl, n-pentyl, n-hexyl, n-octyl, n-decyl, n-dodecyl, n-tetradecyl and n-octadecyl. Examples of cycloalkyl groups represented by $Y_1$ are cyclopropyl, cyclobutyl, cyclopentyl and cyclohexyl.

For illustration purposes some specific examples of compounds of formulae I to IV are mentioned.

Compounds of Formula I
n-hexyl-β-(2-methyl-5-t-butyl-hydroxyphenyl) propionate
n-octyl-β-(3,5-di-t-butyl-4-hydroxyphenyl) propionate
n-decyl-β(3-ethyl-5-t-butyl-4-hydroxyphenyl) propionate
n-hexadecyl-β-(3-n-hexyl-5-isopropyl-5-hydroxyphenyl)propionate
n-octadecyl-62 -(3,5-di-t-butyl-4-hydroxyphenyl) propionate
n-dodecyl-β-(3-ethyl-5-t-butyl-4-hydroxyphenyl) propionate
N-methyl-β-(3,5-di-t-butyl-4-hydroxyphenyl) propionamide
N,N-diethyl-β-(3-methyl-5-isopropyl-4-hydroxyphenyl)propionamide
N-n-hexyl-β-(3,5-di-isopropyl-4-hydroxyphenyl) propionamide
N-n-decyl-β-(3,5-di-t-butyl-4-hydroxyphenyl) propionamide
N-cyclopropyl-β-(3,6-di-t-butyl-4-hydroxyphenyl) propionamide
N-cyclohexyl-β-(3,5-di-t-butyl-4-hydroxyphenyl) propionamide
piperazino-β-(2-ethyl-5-isopropyl-4-hydroxyphenyl) propionamide Compounds of Formula II
ethylene-bis-β-(3,5-di-t-butyl-4-hydroxyphenyl)propionate
isopropylene-bis-β(3-methyl-5-t-butyl-4hydroxyphenyl)propionate
1,4-butylene-bis-β-(3,5-isopropyl-4-hydroxyphenyl)-propionate
1,6-hexylene-bis-β-(3,5-di-t-butyl-4-hydroxyphenyl)-propionate
1,7-heptylene-bis-β-(3,4-di-t-butyl-4-hydroxyphenyl)-propionate
1,8-octylene-bisβ-(3,5-di-t-butyl-4-hydroxyphenyl)propionate
1,2-bis-{3-(3-methyl-5-isopropyl-4-hydroxyphenyl)propionamido}ethane
1,2bis-{3-(3,5-di-t-butyl-4-hydroxyphenyl)propionamido}propane
1,6-bis-{3-(2-ethyl-5-t-butyl-4-hydroxyphenyl)propionamido}hexane
1,8-bis-{3-(3,5-di-t-butyl-4-hydroxyphenyl)propionamido}octane.

Compounds of Formula III
1,1,1-trimethylol-propane-{3-(3',5'-di-t-butyl-4'-hydroxyphenyl)-propionate}
pentaerythritol tetrakis-{3-(2'-methyl-5'-t-butyl-4'-hydroxyphenyl)-propionate}
pentaerythritol tetrakis-{3-(3',5'-di-t-butyl-4'-hydroxyphenyl)-propionate}
tetrakis-{3(3,5-di-t-butyl-4-hydroxyphenyl)propionamidomethyl}methane
tetrakis-(2-{3-(3-methyl-5-isopropyl-4-hydroxyphenyl)-propionamido}ethyl-ethylendiamine Compounds of Formula IV
thio-bis-{ethylene-3(3,5-di-t-butyl-4-hydroxyphenyl)-propionate}
thio-bis-{isopropylene-3-(3,5-di-t-butyl-4-hydroxyphenyl)propionate}

Examples of suitable phenol compounds of Formula V to be used in the improved process according to the invention are:
2-methyl-6-isopropyl-4-hydroxyphenol
2-methyl-2-t-butyl-5-methyl-4-hydroxyphenol
2-methyl-6-t-butyl-4-hydroxyphenol
2-ethyl-2-isopropyl-5-ethyl-4-hydroxyphenol
6-ethyl-6-t-butyl-4-hydroxyphenol
2,6-di-isopropyl-4-hydroxyphenol 2-n-hexyl-6-isopropyl-4-hydroxyphenol 2,6-d-t-butyl-4-hydroxyphenol As illustrative examples of compounds of formulae Ia, Ib, IIa, IIb, IIIa, IIIb and IVa the following may be mentioned:

Monohydric Alcohols
n-hexyl
n-octyl
n-decyl
n-dodecyl
n-hexadecyl
n-octadecyl

Monoamines
N-methylamine
N,N-diethylamine
N,n-propylamine
N-n-hexylamine
N-n-octylamine
N,n-dodecylamine
N-n-octadecylamine
N,n-di-n-hexylamine
N,N-di-n-octylamine
N-cyclopropylamine
N-cyclohexylamine
piperasine Dihydric Alcohols
1,2-ethyleneglycol
1,2-propanediol 1,3-propanediol
1,4-butanediol
2,5-hexanediol
1,6-hexanediol
1,7-heptanediol
1,8-octanediol Diamines
ethylenediamine
1,2-diaminopropane
1,3-diaminopropane
1,4-tetramethylenediamine
1,5-pentamethylenediamine
1,6-hexamethylenediamine
1,8-octamethylenediamine Tri- and Tetrahydric Alcohols
1,1,1-trimethylolpropane
pentaerythritol
N,N,N-tris-(2-aminoethyl)amine
N,N,N-tris-(3-aminopropyl)amine
N,N,N',N'-tetrakis-(aminomethyl)ethylenediamine
N,N,N',N'-tetrakis-(2-aminoethyl)ethylenediamine Thioether Compounds
bis-($\beta$-hydroxyethyl)-sulfide(thiodiglycol)
bis-($\beta$-(hydroxypropyl)sulfide Preferred compounds of Formulae I to IV, and Ia to IVa, respectively, are those wherein $R_1$ and $R_2$ are ortho to the hydroxyl group, each of $R_1$ and $R_2$ being a branched alkyl group, more particularly t-butyl, $B_1$ represents —O—$(C_xH_{2x})$—H and x has a value from 12 to 24, inclusively, $B_2$ represents —O— and y has a value from 2 to 6 inclusively, each of z and z' have a value of 2 or 3, $B_3$ represents —O—$CH_2$— and $B_4''$ represents —C—$CH_2OH$.

The most preferred compounds of Formulae I to IV are n-octadecyl-$\beta$-(3,5-di-t-butyl-4-hydroxyphenyl)-propionate, ethylene-bis-$\beta$(3,5-di-t-butyl-4-hydroxyphenyl)propionate, hexylene-1,6-bis-$\beta$-(3,5-di-t-butyl-4-hydroxyphenyl)propionate, pentaerythritol tetrakis-{3-3',5'-di-t-butyl-4'-hydroxyphenyl)propionate}and thio-bis-{ethylene-3-(3,5-di-t-butyl-4-hydroxyphenyl)propionate}.

Suitable alkaline catalysts to be used in the process of the instant invention are alkali metal hydrides, alkali metal alkoxides of the formula.

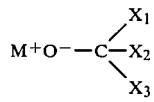

VI' wherein
M is an alkali metal ion, and
$X_1$, $X_2$ and $X_3$ independently of each other represent hydrogen, alkyl, aryl or arylalkyl groups having up to about 12 carbon atoms, and
alkali metal amides of the formula

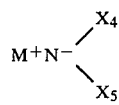

VII wherein
M is as defined above, and
$X_4$ and $X_5$ independently of each other represent hydrogen, alkyl or aryl groups having up to about 12 carbon atoms.

Alkyl radicals represented by $X_1$, $X_2$, $X_3$, $X_4$, and $X_5$ are preferably methyl or ethyl groups, while aryl and arylalkyl radicals designated by one or more of said symbols are, e.g., phenyl, benzyl, or phenethyl groups. Suitable alkali metals are lithium, potassium and sodium.

Examples of suitable alkaline catalysts are thus lithium, sodium and potassium hydrides, sodium and potassium methoxides, ethoxides, propoxides, isopropoxides, t-butoxides, sodium 1,1-dimethylbutoxides, potassium benzyloxide, sodium benzyl-isopropoxide, lithium, potassium and sodium amides, lithium N-methylamide and N-ethylamide, lithium N,N-dimethylamide and sodium N-methyl-N-phenylamide.

Among the alkali metal amides of Formula VII those are preferred wherein M is the sodium or potassium ion and $X_4$ and $X_5$ each represent hydrogen.

It is, however, particularly preferred to employ alkali metal alkoxides or Formula VI as the alkaline catalysts, more especially those wherein M is the sodium or potassium ion, and $X_1$, $X_2$ and $X_3$ each represent hydrogen or $X_1$ represents hydrogen, $X_2$ represents hydrogen or methyl and $X_3$ represents methyl, alkali metal alkoxides of Formula VI being most preferred wherein M is the sodium or potassium ion, and $X_1$, $X_2$ and $X_3$ each represents methyl.

Although the alkaline catalysts may be employed in amounts ranging from 0.001 to 10 mole percent based on the phenol compound of Formula V, amounts of from about 1 to 5 mole percent are preferred.

The gradual addition of methyl acrylate to the phenol compound in the presence of an alkaline catalyst represents a critical feature of the present process. Care should be taken that methyl acrylate is fed to the reaction mixture at a constant slow rate throughout the reaction so as to keep the methyl acrylate concentration in the reaction mixture to a minimum and thereby minimize the formation of undesirable by-products, such as polymers and diesters. Throughout the gradual addition of methyl acrylate and until completion of the reaction, the reaction mixture is conveniently heated to a temperature between about 80° and 140° C., more particularly 100° and 120° C., under nitrogen. The overall molar ratio of methyl acrylate and the phenol compound of Formula V should be at least 1:1; preferably, a slight excess, e.g., an excess of about 5 to 30 mole percent, of methyl acrylate is used. Small amounts of an aliphatic alcohol, such as methyl alcohol, ethyl alcohol or isopropyl alcohol, or a dipolar aprotic solvent, such as dimethylsulfoxide or formamide, may be added to the reaction mixture so as to improve the conversion.

After the completion of the reaction, the reaction mass is advantageously cooled to about 60° to 80° C. Immediately thereafter, a compound of Formulae Ia to IVa is added together with from 0 to 10 mole percent, preferably from 1 to 5 mole percent, of a second alkaline catalyst, different from the first alkaline catalyst, and optionally an inert organic solvent. Suitable inert organic solvents are, e.g., tetrahydronaphthalene (tetraline), toluene, dimethylsulfoxide and dimethylformamide. Any other organic solvent can be employed as long as it is inert in relation to the reactants and preferably has a boiling point in the general area of the reaction temperature.

The purpose of the organic solvent is to act as a reaction medium and also to aid in removing (stripping) methanol from the reaction medium as it is being formed as a by-product of the reaction.

The second alkaline catalyst may be selected from the classes of compounds listed above for the first alkaline catalyst, i.e., alkali metal hydrides, alkali metal alkoxides of Formula VI or alkali metal amides of Formula VII. In addition, alkali metal hydroxides may be employed, such as lithium hydroxide. Preferred second alkaline catalysts are lithium amide and lithium hydroxide.

Finally, the temperature is again raised to about 130° to 160° C. After the completion of the reaction, the resultant ester of Formulae I to IV is isolated and purified by conventional methods, e.g., by acidifying the reaction mass, e.g., with glacial acetic acid and crystallizing the product from a suitable organic solvent such as aliphatic hydrocarbons, e.g., hexane or heptane, and lower aliphatic alcohols, e.g., methyl alcohol, ethyl alcohol and isopropyl, alcohol.

The compounds of Formulae I to IV are obtained in high yields and substantially free from undesirable by-products. These compounds are known per se and can be used for the stabilization of organic materials normally subject to oxidative deterioration according to known procedures.

Materials which can be stabilized with the compounds of Formulae I to IV include synthetic organic polymeric substances such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as polyethylene, polypropylene, polybutylene, polyisoprene and the like, including copolymers of poly-$\alpha$-olefins; polyurethanes prepared from polyols such as propylene glycol or ethylene glycol and organic polyisocyanates; polyamides such as polyhexamethylene adipamide; polyesters such as polymethylene terephthalates; polycarbonates; polyacetals; polystyrene, polyethylene oxide; and copolymers such as those of high impact polystyrene containing copolymers of butadiene and styrene and those formed by the copolymerization of acrylonitrile, butadiene and/or styrene. Other materials which can be stabilized with the compounds of Formulae I to IV include lubricating oils of the aliphatic ester type, e.g., di-(2-ethylhexyl)-azelate, pentaerythritol tetracaproate and the like; animal and vegetable derived oils, e.g., linseed oil, fat, tallow, lard, peanut oil, cod liver oil, castor oil, palm oil, corn oil, cotton seed oil and the like; hydrocarbon materials such as gasoline, both natural and synthetic, diesel oil, mineral oil, fuel oil, drying oil, cutting fluids, waxes, resins and the like, fatty acids such as soaps and the like.

In general, the stabilizer compounds of Formulae I to IV are employed in amounts of from about 0.005% to about 10% by weight of the material to be stablized. A particularly advantageous range for polyolefins such as polypropylene is from about 0.1% to about 1%.

The following examples serve to illustrate the process of this invention.

EXAMPLE 1

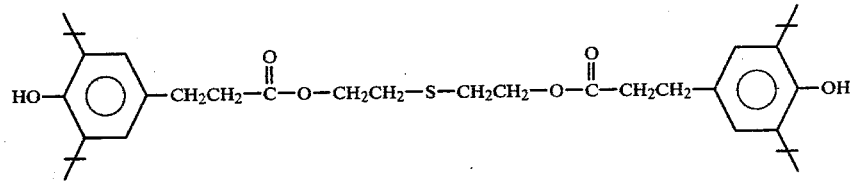

To a 500 ml, 3-necked flask, equipped with a stirrer, a reflux condenser, a calibrated dropping funnel, a thermometer and a nitrogen inlet were charged 103 g of 2,6-di-t-butylphenol. The phenol was heated to 70° C., and the system was purged carefully with nitrogen. Then 1.4 g of potassium t-butoxide were added, followed by 2 ml of isopropyl alcohol. The resultant mixture was heated to 107° C. to 110° C., whereupon 47.3 g of methyl acrylate were added at a uniform rate over a two hour period while maintaining the specified temperature range. The mixture was held for three hours at the specified temperature range. Then vacuum was applied to strip excess methyl acrylate. The vacuum was released with nitrogen, the mixture was cooled to 70° C. and 24.4 g of thiodiglycol were added, followed by 0.47 g of lithium hydroxide monohydrate. Vacuum was applied and the pressure was reduced to 20 mm Hg. The reaction mixture was then gradually heated to 140° to 145° C. in two hours and held at that temperature for three hours. The vacuum was then released with nitrogen, and the reaction mass was cooled to 70° C. and acidified with 3.0 g of glacial acetic acid. 132 g of ethyl alcohol were added to the melt, and the resultant solution was clarified. The filtrate was cooled to 28° C. and seeded with 0.5 g of thio-bis-{ethylene-3-(3,5-di-t-butyl-4-hydroxyphenyl)propionate}.

The reaction product crystallized and the resulting slurry was cooled to 16° C. The product was isolated on a Buchner funnel, washed with cold ethyl alcohol, sucked dry and dried in a vacuum oven at 50° C. to a constant weight. 97.0 g of dry thio-bis- {ethylene-3-(3,5-di-t-butyl-4-hydroxyphenyl)propionate} were obtained; m.p. 71.5° C.; yield 75.4%, based on the thiodiglycol employed.

Similar results are obtained if, in the above example, instead of 1.4 g of potassium t-butoxide as a first catalyst equivalent amounts of sodium or potassium methoxide are used and lithium hydroxide monohydrate (second catalyst) is replaced by an equivalent amount of lithium amide.

EXAMPLE 2

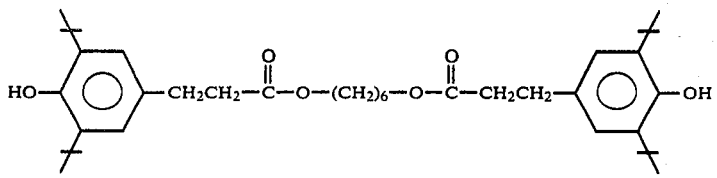

Following the procedure described in Example 1, except for using 23.6 g of 1,6-hexanediol in place of thiodiglycol, hexylene-1,6-bis-β-(3,5-di-t-butyl-4-hydroxyphenyl)propionate is obtained in good yields.

EXAMPLE 3

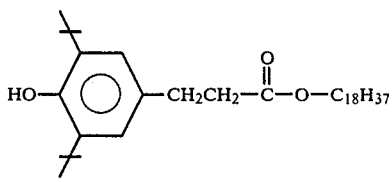

The procedure described in Example 1 was followed using, however, 126 g of n-octadecyl alcohol in place of thiodiglycol and crystallizing the reaction product from 750 g of 90% isopropyl alcohol. 218 g of dry n-octadecyl-β-(3,5-di-t-butyl-4-hydroxyphenyl)propionate were obtained; m.p. 53.0° C.; yield 87% based on the n-octadecyl alcohol employed.

EXAMPLE 4

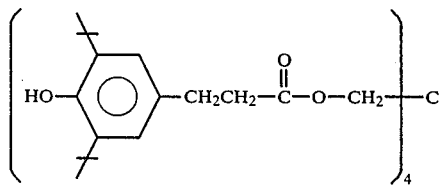

To a 1000 ml 3-necked flask, equipped with a stirrer, a reflux condenser, a calibrated dropping funnel, a thermometer and a nitrogen inlet were charged 250 g of 2,6di-t-butylphenol. The phenol was melted, the system was purged with nitrogen, and at 45° C. 1.65 g. of sodium methoxide was added. The reaction mixture was then heated to 104° C. and 109.5 g of methyl acrylate were added dropwise at 100° to 104° C. over two hours. The mixture was held for four hours at approximately 100° C. to complete the conversion. Vacuum was applied to strip excess of methyl acrylate. The vacuum was then released with nitrogen and at 65° C. 34 g of pentaerythritol were added to the melt. The reaction melt was heated to 105° C. and a suspension made from 0.38 g of ground lithium amide and 9.5 g of tetralin was charged. The water circulated through the condenser jacket was at 60° C. Vacuum was applied and the pressure was reduced to 8 to 20 mm Hg. while heating the mixture in 2.5 hours 155° C. and holding it at that temperature for nine hours. The vacuum was released with nitrogen. The reaction mixture was cooled to 110° C. and acidified with 3.0 g of glacial acetic acid. The resultant melt was dissolved in 500 ml of ethyl alcohol, and the solution was clarified into a 2000 ml flask. 445 ml of ethyl alcohol were added to the filtrate and the solution was seeded with 0.5 g of pentaerythritol tetrakis-{3-(3',5'-di-t-butyl-4-hydroxypheny)propionate} at 40° C. The reaction product crystallized, and the slurry was allowed to cool overnight. The reaction product was then isolated on a Buchner funnel, washed with ethyl alcohol, sucked dry and dried in a vacuum oven at 60° C. to a constant weight. 114 g of dry pentaerythritol tetrakis-{3-(3',5'-di-t-butyl-4-hydroxyphenyl)propionate} of the above formula were obtained.

EXAMPLE 5

Following the procedure described in Example 4, omitting, however, addition of the second catalyst (lithium amide) and extending the overall reaction time after the addition of pentaerythritol from 11.5 to about 15 hours, pentaerythritol tetrakis-{3-(3',5'-di-t-butyl-4-hydroxyphenyl)-propionate} is obtained in similar yields.

EXAMPLE 6

Example 3 was repeated, using, however, instead of 1.4 g of potassium t-butoxide and 2 ml of isopropyl alcohol, 1.4 g of sodium methoxide and replacing the 0.47 g of lithium hydroxide monohydrate by 0.3 g of lithium amide. 211 g of dry n-octadecyl-β-(3,5-di-t-butyl-4-hydroxyphenyl) propionate were obtained; yield 84% based on the n-octadecyl alcohol employed.

EXAMPLE 7

Example 3 was repeated, except that 0.72 g of glacial acetic acid was added after stripping off the excess methyl acrylate. 211 g of dry n-octadecyl-β-(3,5-di-t-butyl-4-hydroxphenyl)propionate were obtained; yield 84% based on the n-octadecyl alcohol employed.

What is claimed is:

1. An improved process for the production of a compound having the formula I

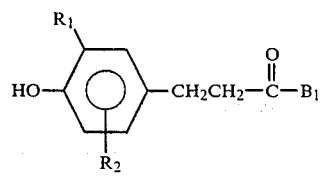

wherein
$R_1$ and $R_2$ independently represent an alkyl group having from 1 to 6 carbon atoms,
$B_1$ represents $-O-(C_xH_{2x})-H$ or

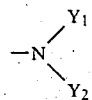

wherein x has a value from 6 to 30, inclusively, $Y_1$ represent an alkyl group having from 1 to 18 carbon atoms or a cycloalkyl group having from 5 to 12 carbon atoms and $Y_2$ represents hydrogen or an alkyl group having from 1 to 18 carbon atoms, a cycloalkyl group of 5 to 12 carbon atoms, or $Y_1$ and $Y_2$ together with the nitrogen atoms to which they are linked form a piperidino ring, which process comprises gradually adding methyl acrylate to a phenol compound of the formula

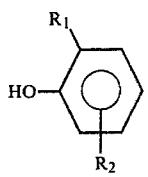  V wherein $R_1$ and $R_2$ are as defined above, in the presence of from 0.001 to 10 mole percent, based on the phenol compound, of an alkaline catalyst, and, after completion of the reaction, adding to the resultant reaction mixture a compound selected from (a) a monohydric alcohol or a monoamine of the formulae

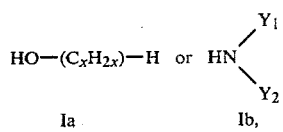

Ia    Ib, wherein x, $Y_1$ and $Y_2$ are as defined above, the second reaction being carried out in the presence of from 0 to 10 mole percent of a second alkaline catalyst which is different from the first catalyst.

2. An improved process for the production of a compound having the formula II

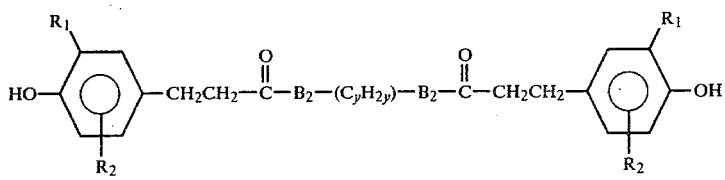 II, wherein $R_1$ and $R_2$ independently represent an alkyl group having from 1 to 6 carbon atoms, $B_2$ each represent —O— or —NH— and y has a value from 2 to 18 inclusively, which process comprises gradually adding methyl acrylate to a phenol compound of the formula

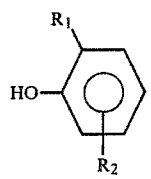 V wherein $R_1$ and $R_2$ are as defined above, in the presence of from 0.001 to 10 mole percent, based on the phenol compound, of an alkaline catalyst, and, after completion of the reaction, adding to the resultant reaction mixture a compound selected from (b) a dihydric alcohol or a diamine of the formula

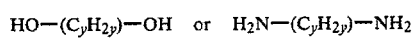

IIa    IIb, wherein y is as defined above, the second reaction being carried out in the presence of from 0 to 10 mole percent of a second alkaline catalyst which is different from the first catalyst.

3. An improved process for the production of a compound having the formula III

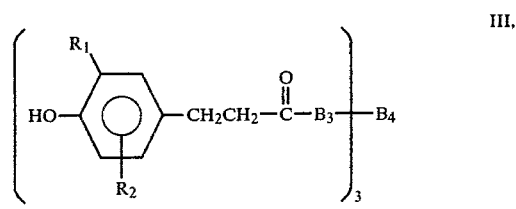 III, wherein $R_1$ and $R_2$ independently represent an alkyl group having from 1 to 6 carbon atoms, $B_3$ represents —O—$CH_2$— and $B_4$ represents

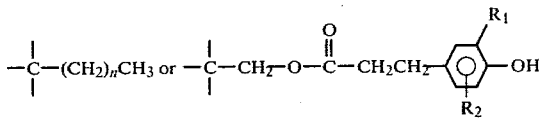

wherein $R_1$ and $R_2$ are as defined above, and n is 0 to 6 or $B_3$ represents —NH—$(CH_2)_m$— and $B_4$ represents

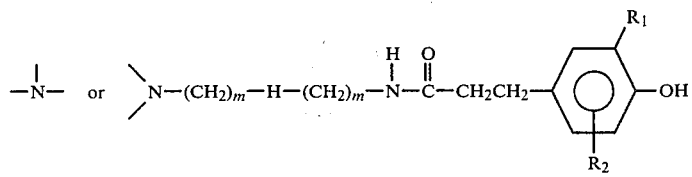

wherein m has a value from 2 to 6 and $R_1$ and $R_2$ are as defined above, and which process comprises gradually adding methyl acrylate to a phenol compound of the formula

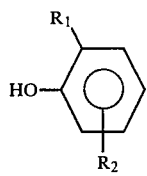
V wherein $R_1$ and $R_2$ are as defined above, in the presence of from 0.001 to 10 mole percent, based on the phenol compound, of an alkaline catalyst, and, after completion of the reaction, adding to the resultant reaction mixture a compound selected from
(c) a tri- or tetrahydric alcohol or a polyamine of the formula $$(HO{-}B_3\!\!\overline{\phantom{x}}\!\!\overline{\phantom{x}}\!\!B_4' \quad \text{or} \quad (NH_2{-}B_3\!\!\overline{\phantom{x}}\!\!\overline{\phantom{x}}\!\!B_4''$$
$$\text{IIIa} \qquad\qquad \text{IIIb,}$$

wherein
$R_1$, $R_2$ and $B_3$, are as defined above,
$B_4'$ represents

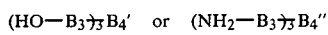

and
$B_4''$ represents

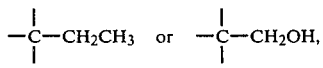

wherein m is as defined above, the second reaction being carried out in the presence of from 0 to 10 mole percent of a second alkaline catalyst which is different from the first catalyst.

4. An improved process for the production of a compound having the formula IV

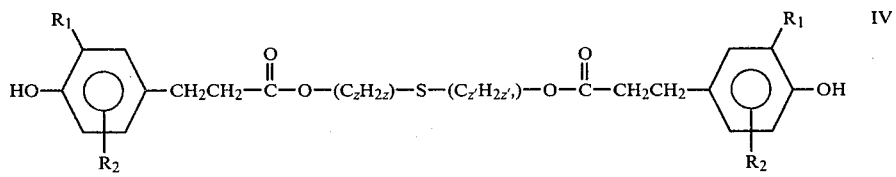

wherein
$R_1$ and $R_2$ independently represent an alkyl group having from 1 to 6 carbon atoms,
each of z and z′ have a value from 2 to 12, inclusively, which process gradually adding methyl acrylate to a phenol compound of the formula

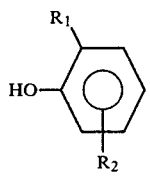
V wherein $R_1$ and $R_2$ are as defined above, in the presence of from 0.001 to 10 mole percent, based on the phenol compound, of an alkaline catalyst, and, after completion of the reaction, adding to the resultant reaction mixture a compound selected from
(d) a thioether compound of the formula $$HO{-}(C_zH_{2z}){-}S{-}(C_{z'}H_{2z'}){-}OH \qquad \text{IVa}$$

wherein z and z′ are as defined above, the second reaction being carried out in the presence of from 0 to 10 mole percent of a second alkaline catalyst which is different from the first catalyst.

5. A process as claimed in claims 1, 2 or 3 or 4 characterized by using as the alkaline catalyst a compound selected from alkali metal hydrides, alkali metal alkoxides of the formula

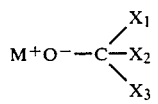
VI′ wherein
M is an alkali metal ion, and
$X_1$, $X_2$ and $X_3$ independently of each other represent hydrogen, alkyl, aryl or aryalkyl groups having up to about 12 carbon atoms, and
alkali metal amides of the formula

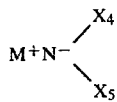

wherein
M is as defined above, and
X$_4$ and X$_5$ independently of each other represents hydrogen, alkyl or aryl groups having up to about 12 carbon atoms.

6. A process as claimed in claim 5 characterized by using an alkali metal alkoxide of formula VI, wherein M is the sodium or potassium ion, and X$_1$, X$_2$ and X$_3$ each represent hydrogen or X$_1$ represents hydrogen, X$_2$ represents hydrogen or methyl and X$_3$ represents methyl.

7. A process as claimed in claim 5 characterized by using an alkali metal alkoxide of formula VI, wherein N is the sodium or potassium ion, and X$_1$, X$_2$ and X$_3$ each represent methyl.

8. A process as claimed in claim 1 for the production of compounds of Formula I, wherein R$_2$ is in the ortho position to the hydroxyl group and each of R$_1$ and R$_3$ represents a branched alkyl group, and R$_1$ represents —O—(C$_x$N$_{2x}$)—N, which comprises gradually adding methyl acrylate to a phenol of Formula V wherein R$_2$ is in the ortho position to the hydroxy group and each of R$_1$ and R$_2$ represents a branched alkyl group and adding to the resultant reaction mixture a monohydric alcohol of Formula Ia wherein x is as defined in claim 1.

9. A process as claimed in claim 8 wherein R$_1$ and R$_2$ each represent t-butyl and x has a value from 12 to 24 inclusively, the phenol of Formula VI is 2,5-di-t-butylphenol, and in the monohydric alcohol of Formula Ia, x has a value from 12 to 24, inclusively.

10. A process as claimed in claim 1 for the production of n-octadecyl-β-(3,5-di-t-butyl-4-hydroxyphenyl)propionate, which comprises gradually adding methyl acrylate to 2,6-di-t-butylphenol, and adding to the resultant reaction mixture n-octadecyl alcohol.

11. A process as claimed in claim 2 for the production of compounds of Formula II, wherein R$_2$ is in the ortho position to the hydroxyl group and each of R$_1$ and R$_2$ represents a branched alkyl group, and R$_2$ represents —O—, which comprises gradually adding methyl acrylate to a phenol of Formula V wherein R$_2$ is in the ortho position to the hydroxyl group and each of R$_1$ and R$_2$ represents a branched alkyl group and adding to the resultant reaction mixture a dihydric alcohol of Formula IIb wherein y is as defined in claim 2.

12. A process as claimed in claim 11 wherein R$_1$ and R$_2$ each represent t-butyl, y has a value from 2 to 6, inclusively, the phenol of Formula V is 2,6-di-t-butylphenol and in the dihydric alcohol of Formula IIa has a value from 2 to 6, inclusively.

13. A process as claimed in claim 2 for the production of ethylene-bis-β-(3,5-di-t-butyl-4-hydroxyphenyl)propionate or hexylene-1,2-bis-β-(3,5-di-t-butyl-4-hydroxyphenyl)propionate, which comprises gradually adding methyl acrylate to 2,6-di-t-butylphenol and adding 1,2-ethyleneglycol or 1,6-hexanediol to the resultant reaction mixture.

14. A process as claimed in claim 3 for the production of compounds of Formula III wherein R$_2$ is in the ortho position to the hydroxyl group and each of R$_1$ and R$_2$ represents a branched alkyl group, R$_3$ represents —O—CH$_2$—, B$_4$ represents —C—CH$_2$CH$_3$ or

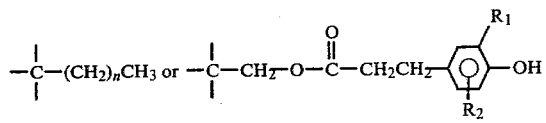

and R$_1$ and R$_2$ are as defined above, which comprises gradually adding methyl acrylate to a phenol of Formula V, wherein R$_2$ is in the ortho position to the hydroxyl group and each of R$_1$ and R$_2$ represents a branched alkyl group and adding to the resultant reaction mixture a tri- or tetrahydric alcohol of Formula IIIa wherein R$_3$ and R$_4'$ are as defined in claim 3.

15. A process as claimed in claim 14 wherein R$_2$ is in the ortho position to the hydroxyl group, R$_1$ and R$_2$ each represent t-butyl, and the phenol of Formula V is 2,6-di-t-butylphenol.

16. A process as claimed in claim 3 for the production of pentaerythritol tetrakis-{3-(3',5'-di-t-butyl-4'-hydroxyphenyl)propionate}), which comprises gradually adding methyl acrylate to 2,6-di-t-butylphenol, and adding pentaerythritol to the resultant reaction mixture.

17. A process as claimed in claim 3 for the production of compounds of Formula IV, wherein R$_2$ is in the ortho position to the hydroxyl group, and each of R$_1$ and R$_2$ represent a branched alkyl group, which comprises gradually adding methyl acrylate to a phenol of Formula V wherein R$_2$ is in the ortho position to the hydroxyl group and R$_1$ and R$_2$ each represent a branched alkyl group.

18. A process as claimed in claim 14 wherein each of R$_1$ and R$_2$ represents t-butyl, each of s and s' have a value of 2 or 3, the phenol is 2,6-di-t-butylphenol, and in the thioether of Formula IVa, s and s' have a value of 5 or 6.

19. A process as claimed in claim 4 for the production of thio-bis-{ethylene-3-(3,5-di-t-butyl-4-hydroxyphenyl)propionate}, which comprises gradually adding methyl acrylate to 2,6-di-t-butylphenol and adding thiodiglycol to the resultant reaction mixture.

* * * * *